(12) United States Patent
Janzig et al.

(10) Patent No.: US 11,890,484 B2
(45) Date of Patent: *Feb. 6, 2024

(54) IMPLANTABLE MEDICAL DEVICES HAVING MODULAR LEAD BORES

(71) Applicant: MEDTRONIC, INC., Minneapolis, MN (US)

(72) Inventors: Darren A. Janzig, Center City, MN (US); Andrew Thom, Maple Grove, MN (US); Brad Tischendorf, Minneapolis, MN (US); Randy S. Roles, Elk River, MN (US); Steven T. Deininger, Plymouth, MN (US); Nicholas R. Whitehead, Lake Elmo, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/086,224

(22) Filed: Dec. 21, 2022

(65) Prior Publication Data

US 2023/0127724 A1    Apr. 27, 2023

Related U.S. Application Data

(63) Continuation of application No. 16/717,912, filed on Dec. 17, 2019, now Pat. No. 11,559,695.

(51) Int. Cl.
*A61N 1/375* (2006.01)

(52) U.S. Cl.
CPC ....... *A61N 1/3754* (2013.01); *A61N 1/37514* (2017.08)

(58) Field of Classification Search
CPC .................. A61N 1/3754; A61N 1/37514
See application file for complete search history.

(56) References Cited

U.S. PATENT DOCUMENTS

| 4,848,346 A | 7/1989 | Crawford |
| 6,878,013 B1 | 4/2005 | Behan |
| 6,895,276 B2 | 5/2005 | Kast et al. |

(Continued)

OTHER PUBLICATIONS

European Application No. 20215079.3 Search Report, dated May 4, 2021.

*Primary Examiner* — Ankit D Tejani
*Assistant Examiner* — Joshua Brendon Solomon
(74) *Attorney, Agent, or Firm* — WITHERS & KEYS, LLC

(57) ABSTRACT

Implantable medical devices have modular lead bores that are constructed from individual lead bore modules. A given modular lead bore utilizes the number of individual lead bore modules necessary for the particular implantable medical device. Each lead bore module has a lead bore passageway and a feedthrough passageway. An electrical contact is present within the lead bore passageway of each lead bore module and the electrical contact is aligned to the lead bore passageway of a lead bore module. Hermetic feedthrough assemblies are also present within the lead bore passageway of each lead bore module. A feedthrough pin passes through a hermetic feedthrough assembly within a feedthrough passageway of each lead bore module. Each feedthrough pin is electrically coupled to a corresponding electrical contact and the medical device circuitry.

15 Claims, 8 Drawing Sheets

(56) References Cited

U.S. PATENT DOCUMENTS

| | | |
|---|---|---|
| 7,070,455 B2 | 7/2006 | Balsells |
| 7,195,523 B2 | 3/2007 | Naviaux |
| 7,812,691 B1 | 10/2010 | Fisk et al. |
| 7,890,175 B1 | 2/2011 | Rey et al. |
| 8,167,660 B2 | 5/2012 | Dilmaghanian et al. |
| 8,206,175 B2 | 6/2012 | Boyd et al. |
| 8,437,855 B2 | 5/2013 | Sjostedt et al. |
| 8,600,507 B2 | 12/2013 | Brase et al. |
| 9,172,192 B2 | 10/2015 | Seeley et al. |
| 9,233,239 B2 | 1/2016 | Rebentisch et al. |
| 9,345,894 B2 | 5/2016 | Sweeney et al. |
| 10,232,186 B2 | 3/2019 | Sweeney et al. |
| 11,559,695 B2 * | 1/2023 | Janzig ................ A61N 1/3752 |
| 2003/0163171 A1 | 8/2003 | Kast |
| 2005/0186829 A1 | 8/2005 | Balsells |
| 2006/0161215 A1 | 7/2006 | Naviaux |
| 2006/0224208 A1 | 10/2006 | Naviaux |
| 2008/0246231 A1 | 10/2008 | Sjostedt et al. |
| 2009/0192578 A1 | 7/2009 | Biggs |
| 2011/0104955 A1 | 5/2011 | Seeley et al. |
| 2011/0184480 A1 | 7/2011 | Kast et al. |
| 2012/0165902 A1 | 6/2012 | Sommer et al. |
| 2015/0251011 A1 * | 9/2015 | Ranpura ................ H01R 24/00 607/116 |

\* cited by examiner

IMPLANTABLE MEDICAL DEVICES HAVING MODULAR LEAD BORES

TECHNICAL FIELD

The present application relates to implantable medical devices and more particularly to implantable medical devices and extensions that include modular lead bores that receive implantable medical leads.

BACKGROUND

Implantable medical devices that provide therapy including electrical stimulation and/or physiological sensing are typically implanted in a location that can best accommodate the device which may be spaced from the site where the therapy should be applied. An implantable medical lead is implanted with a distal end at the therapy site while the proximal end extends either to the implantable medical device or to a distal end of an implantable lead extension that has a proximal end that extends to the implantable medical device. The implantable medical device includes a lead bore that receives the proximal end of the lead or lead extension. Conductors within the lead and lead extension carry electrical signals between electrodes on the distal end, or contacts on the distal end of the lead extension, and connectors on the proximal end.

Within the lead bore of the implantable medical device, there are electrical contacts that physically and electrically couple to the conductive connectors on the proximal end of the implantable medical lead. These electrical contacts are electrically coupled to circuitry within a hermetically sealed enclosure of the medical device by a feedthrough assembly. The feedthrough assembly provides a conductive path from each of the electrical contacts to the circuitry while providing a hermetic seal to the conductive path, such as by having a conductor pass through a ferrule filled with a glass that is bonded to both the ferrule and the conductor to provide the hermetic seal. This hermetic seal prevents any fluids that may enter the lead bore from entering the enclosure that contains the circuitry.

While the conventional feedthrough assembly is effective for conducting the electrical signals while preventing the ingress of body fluid into the enclosure that contains the circuitry, the conventional feedthrough assembly is typically device specific where the size, position, and number of hermetic seals and conductors of the feedthrough assembly is dependent upon the particular features of a given device or is oversized to meet the needs of the most feature rich device and on other devices some of the conductors are unused. Therefore, providing a device specific feedthrough assembly generally requires additional design and manufacturing efforts for a given device.

SUMMARY

Embodiments address issues such as these and others by providing a modular lead bore for implantable medical devices. The modular lead bore includes a lead bore module for each contact, where each lead bore module includes a hermetic feedthrough assembly. Thus, for a given number of contacts of a device, the modular lead bore is constructed by including the number of lead bore modules needed to achieve the desired number of contacts, and no separate feedthrough for purposes of electrically coupling to the lead or lead extension is required because each lead bore module provides its own hermetic feedthrough assembly.

Embodiments provide an implantable medical device that includes a housing enclosing medical device circuitry and includes a modular lead bore hermetically and mechanically coupled to the housing. The modular lead bore includes a plurality of lead bore modules that are hermetically coupled together, each lead bore module of the plurality of lead bore modules comprising a lead bore passageway and a feedthrough passageway. The modular lead bore includes a plurality of electrical contacts, each electrical contact of the plurality of electrical contacts being aligned to the lead bore passageway of each corresponding lead bore module. The module lead bore includes a plurality of seals, where each seal of the plurality is present within the lead bore passageway of each corresponding lead bore module and between electrical contacts. The modular lead bore includes a plurality of hermetic feedthrough assemblies, each hermetic feedthrough assembly of the plurality of hermetic feedthrough assemblies being present within the feedthrough passageway of each corresponding lead bore module. The module lead bore also includes a plurality of feedthrough pins, with each feedthrough pin of the plurality of feedthrough pins passing through the hermetic feedthrough assembly of each corresponding lead bore module, each feedthrough pin being electrically coupled to the electrical contact of each corresponding lead bore module and the medical device circuitry.

Embodiments provide an implantable medical system that includes an implantable medical device. The implantable medical device includes a housing enclosing medical device circuitry and further comprises a modular lead bore hermetically and mechanically coupled to the housing, the modular lead bore comprising. The implantable medical device also includes a plurality of lead bore modules that are hermetically coupled together, each lead bore module comprising a lead bore passageway and a feedthrough passageway. The modular lead bore includes a plurality of electrical contacts with each electrical contact of the plurality of electrical contacts being present within the lead bore passageway of each corresponding lead bore module. The modular lead bore includes a plurality of seals, where each seal of the plurality is present within a lead bore passageway of each corresponding lead bore module and between electrical contacts. The modular lead bore includes a plurality of hermetic feedthrough assemblies, where each hermetic feedthrough assembly of the plurality of hermetic feedthrough assemblies is present within the feedthrough passageway of each corresponding lead bore module. The modular lead bore also includes a plurality of feedthrough pins, each feedthrough pin of the plurality of feedthrough pins passing through the hermetic feedthrough assembly of the corresponding lead bore module. Each feedthrough pin is electrically coupled to the electrical contact of each corresponding lead bore module and the medical device circuitry. The implantable medical system further includes an implantable medical lead having a proximal end with proximal connectors and a distal end with electrodes. The proximal connectors are electrically coupled to corresponding distal electrodes, and each proximal connector is coupled to the electrical contact of a corresponding lead bore module of the plurality of lead bore modules.

Embodiments provide a method of constructing an implantable medical device that includes providing a housing that encloses medical device circuitry. The method includes creating a hermetic and mechanical coupling of a modular lead bore to the housing. The modular lead bore includes a plurality of lead bore modules that are hermetically coupled together, each lead bore module comprising a lead bore passageway and a feedthrough passageway. The modular lead bore includes a plurality of electrical contacts with each electrical contact of the plurality of electrical contacts being present within the lead bore passageway of each corresponding lead bore module. The modular lead bore includes a plurality of seals, where each seal of the plurality of seals is present the lead bore passageway of each corresponding lead bore module and is present between electrical contacts. The modular lead bore includes a plurality of hermetic feedthrough assemblies, each hermetic feedthrough assembly of the plurality of hermetic feedthrough assemblies being present within the feedthrough passageway of each corresponding lead bore module. The modular lead bore also includes a plurality of feedthrough pins, each feedthrough pin of the plurality of feedthrough pins passing through the hermetic feedthrough assembly of each corresponding lead bore module. Each feedthrough pin of the plurality of feedthrough pins is electrically coupled to the electrical contact of each corresponding lead bore module and the medical device circuitry.

DETAILED DESCRIPTION

Embodiments provide implantable medical devices that include a modular lead bore. The modular lead bore is constructed of individual lead bore modules, each having a hermetic feedthrough assembly. Thus, the lead bore of a given number of contacts can be constructed by utilizing the number of lead bore modules necessary to achieve the number of contacts desired and without providing a separate feedthrough assembly.

Figure 1:
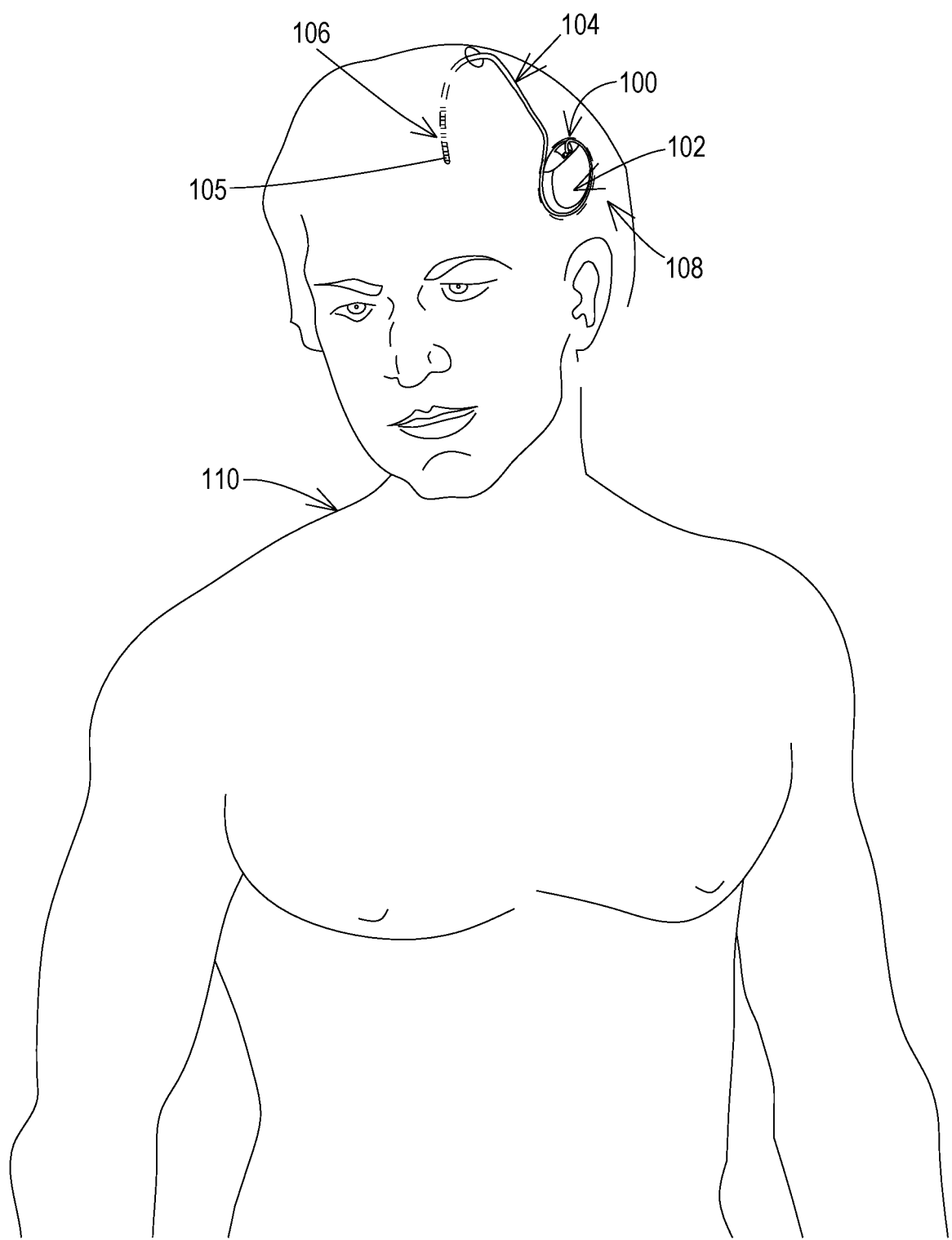
FIG. 1 shows an example of the implantation site for an embodiment of a medical system.

FIG. 1 shows an example of a medical system 100 that has been implanted into a patient 110. In this example, the patient is receiving deep brain stimulation therapy which provides electrical stimulation and/or sensing at a therapy site within the brain. It will be appreciated that embodiments of the medical system 100 may be used for other purposes and in other locations within the body of the patient 110. For instance, the medical system may be used for other forms of neurological stimulation and/or sensing such as spinal cord sensing and/or stimulation, peripheral nerve sensing and/or stimulation, as well as cardiac sensing and/or stimulation, and the like.

The medical system 100 includes a medical device 102 and a medical lead 104 that is coupled to the medical device 102. In this example, the medical device 102 is implanted directly onto the skull of the patient 110. An area 108 may be prepared on the skull to create a depression for the positioning of the medical device 102 subcutaneously in the area 108. This allows the medical device 102 to be positioned much closer to the hole within the skull where the lead 104 is inserted compared to a typical implantation site near the clavicle so that no lead extension is needed in this example. However, it will be appreciated that the medical device 102 may be implanted in other positions, such as near the clavicle for a brain or cardiac therapy site or in the abdomen, lower back, or buttocks regions for other types of stimulation such as spinal cord or pelvic therapy sites. Additionally, the implantable medical system 100 may include a lead extension between the implantable medical device 102 and the implantable medical lead 104 to span any additional distance created by the implantation site of the implantable medical device relative to the therapy site.

As shown in the example of FIG. 1, the medical lead 104 extends from the medical device 102 to the insertion hole within the skull for purposes of providing therapy at the site within the brain. The medical lead 104 extends through the brain to where distal end 106 of the lead 104 having electrodes 105 reaches the therapy site. The medical device 102 being located on the skull may then exchange stimulation and/or sensing signals with the electrodes 105 that have established an electrical interface to the brain tissue.

While this example of FIG. 1 shows a percutaneous lead 104 implanted within the brain of the patient 110, it will be appreciated as previously stated that the medical system 100 that includes the medical device 102 may be implanted in many other areas of the body of the patient 110 while utilizing aspects of the embodiments disclosed herein. It will also be appreciated that other variations in the medical system 100 may exist, such as utilizing other types of leads including paddle-style leads and the like.

Figure 2:
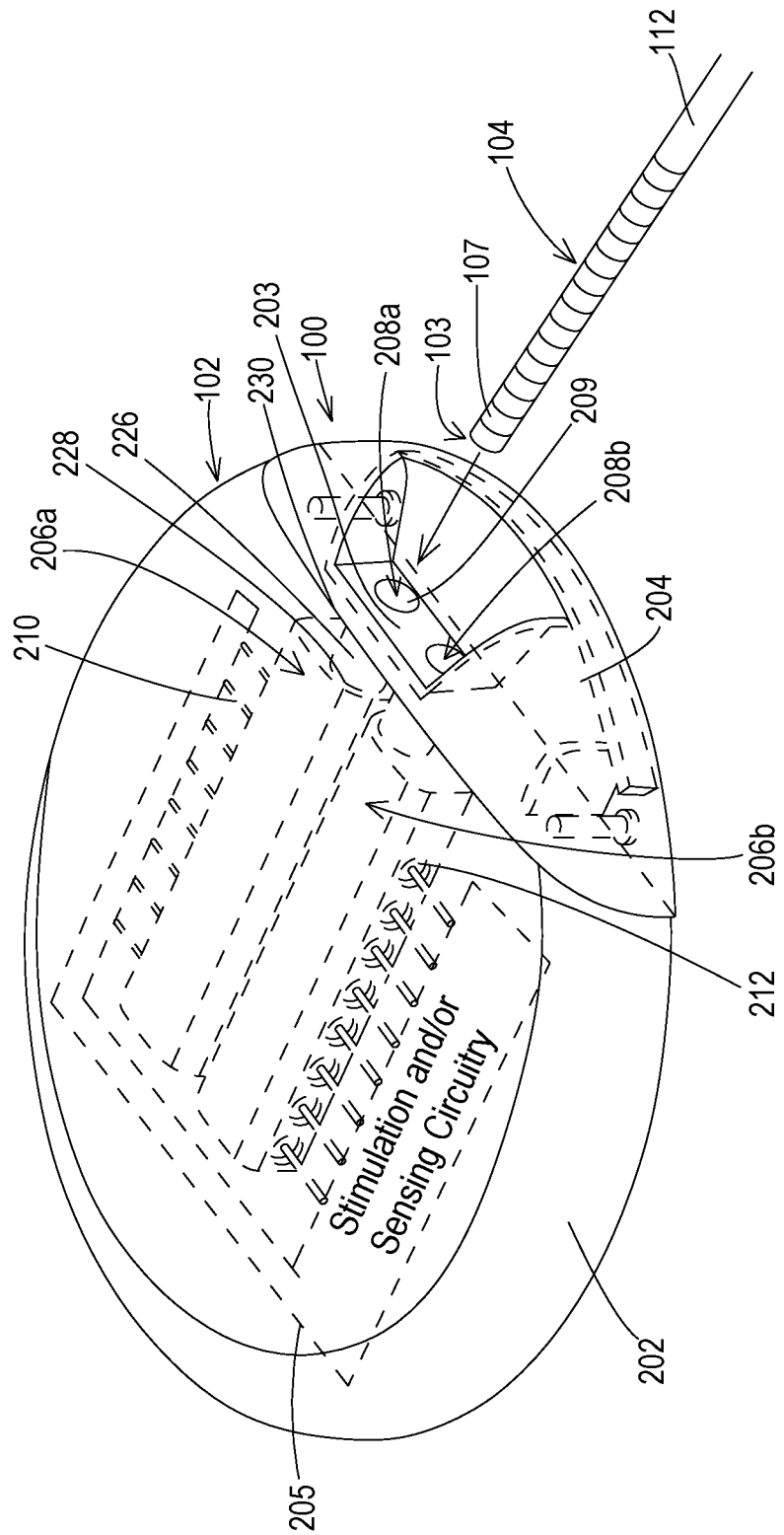
FIG. 2 shows a top perspective view of an example of a medical system where a lead is being inserted into an embodiment of a medical device that includes first and second modular lead bores.

FIG. 2 provides a more detailed view of an example of the medical device 102. Here, it can be seen that the medical device 102 includes an outer enclosure 202. This enclosure 202 provides a hermetic enclosure for the stimulation and/or sensing circuitry 205. To provide such a hermetic enclosure, the enclosure 202 may be constructed of materials such as titanium and titanium alloys. Where the enclosure 202 is constructed of a conductive material such as a metal, the stimulation and sensing circuitry is physically isolated from the enclosure 202, although the stimulation and sensing circuitry may have an electrical connection to the enclosure 202 for purposes of utilizing the enclosure 202 as an electrical node for the stimulation and/or sensing signals when in a unipolar mode.

In the example of the medical device 102 shown in FIG. 2, there may be a header 204 mounted onto the enclosure 202, abutting a wall 203 of the enclosure 202 which is present behind the header 204 in FIG. 2. The header 204 may be present to aid in the insertion and strain relief of the proximal end 103 of the lead 104 or extension being inserted into a lead bore. The combination of the header 204 and the wall 203 of the enclosure 202 form openings 209 to each of two modular lead bores 208a and 208b of this example. It will be appreciated that two lead bores 208a, 208b are shown for purposes of illustrating one example, and that other examples of the medical device 102 may include only a single lead bore or may include more than two lead bores.

While the example of the medical device 102 shown in FIG. 2 has a round disc-like shape, it will be appreciated that the medical device 102, including the enclosure 202 together with the header 204, may have many other shapes in other examples while providing one or more modular lead bores 208a, 208b. Thus, the round disc-like shape is shown only for purposes of illustrating one example.

As shown in FIG. 2, the proximal end 103 of the medical lead 104 is being inserted through the opening 209 and into the modular lead bore 208a. The proximal end 103 of the lead 104 includes several proximal connectors 107, in the form of connector rings in this example, attached to a lead body 112 that establish electrical connections with contacts, discussed in more detail below, that are within the modular lead bore 208a, 208b. The proximal connectors 107 are electrically connected by internal conductors of the lead 104 with the distal electrodes 105, in the form of electrode rings in this example, as shown in FIG. 1. Once the proximal end 103 is fully inserted, the lead 103 may be secured in place by various techniques such as a standard set screw block (not shown) that includes a set screw that tightens against the proximal end 103, such as against one of the proximal connectors 107.

In this example, each modular lead bore 208a, 208b includes a tube 226 that has a first end 230 attached to front wall 203 of the enclosure 202, such as by welding, to form a hermetic seal between the end 230 and the front wall 203. The tube 226 is positioned so as to align with the opening 209 to allow the proximal end 103 of the lead 104 to pass through the opening 209 and through the tube 226 when being inserted into the modular lead bore 208a, 208b. A second end 228 of the tube 226 is either integral with the adjacent module of the modular lead bore assembly 206a, 206b or is attached to the adjacent module of the modular lead bore assembly 206a, 206b, such as by welding, to form a hermetic coupling or seal and a mechanical coupling between the end 228 and the modular lead bore assembly 206a, 206b. Alternatively, the tube 226 may be omitted and the end module of the modular lead bore assembly 206a, 206b may be directly mechanically and hermetically coupled to the front wall 203. As another alternative, the modular lead bore assemblies 206a, 206b can be designed as a portion of the enclosure 202 of the device 102 such as by adjoining the side of enclosure 202 to provide a mechanical and hermetic coupling and which can also provide mechanical flexural protection to the device 102.

The modular lead bore assemblies 206a, 206b are constructed of several individual lead bore modules, which are discussed in more detail below with reference to FIGS. 3A-7. Each lead bore module of the modular lead bore assemblies 206a, 206b includes a feedthrough passageway 212 that includes a hermetic feedthrough assembly, also discussed in more detail below. Each lead bore module also includes a feedthrough pin 210 that passes through the feedthrough passageway 212 by passing through the hermetic feedthrough assembly. Therefore, the feedthrough passageway 212 and feedthrough pin 210 of each lead bore module are made hermetic by the hermetic feedthrough assembly. As shown, the feedthrough pin 210 extends to make contact with and thereby be electrically coupled to the stimulation and/or sensing circuitry 205 within the enclosure. Thus, by the hermetic nature of the ends 228, 230 of the tube 226 as well as the hermetic nature of the lead bore module assemblies 206a, 206b which are also hermetically sealed on the end opposite the tube 226 and include hermetic feedthrough assemblies for the corresponding feedthrough pins 210, the hermeticity of the enclosure 202 is maintained.

Figure 3A:
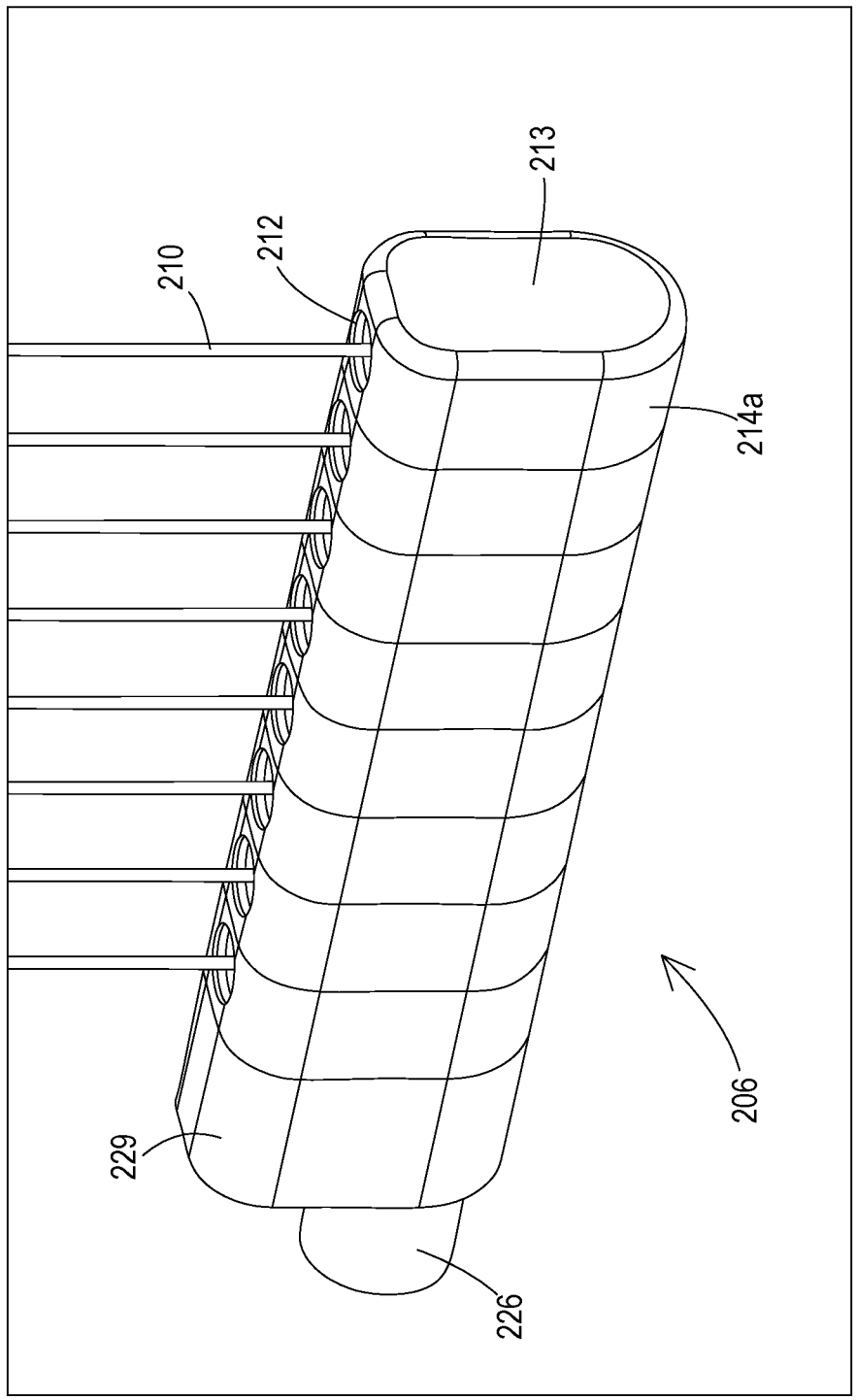
FIG. 3A shows an example of the module lead bore including multiple lead bore modules with an end module providing a hermetic termination.
Figure 3B:
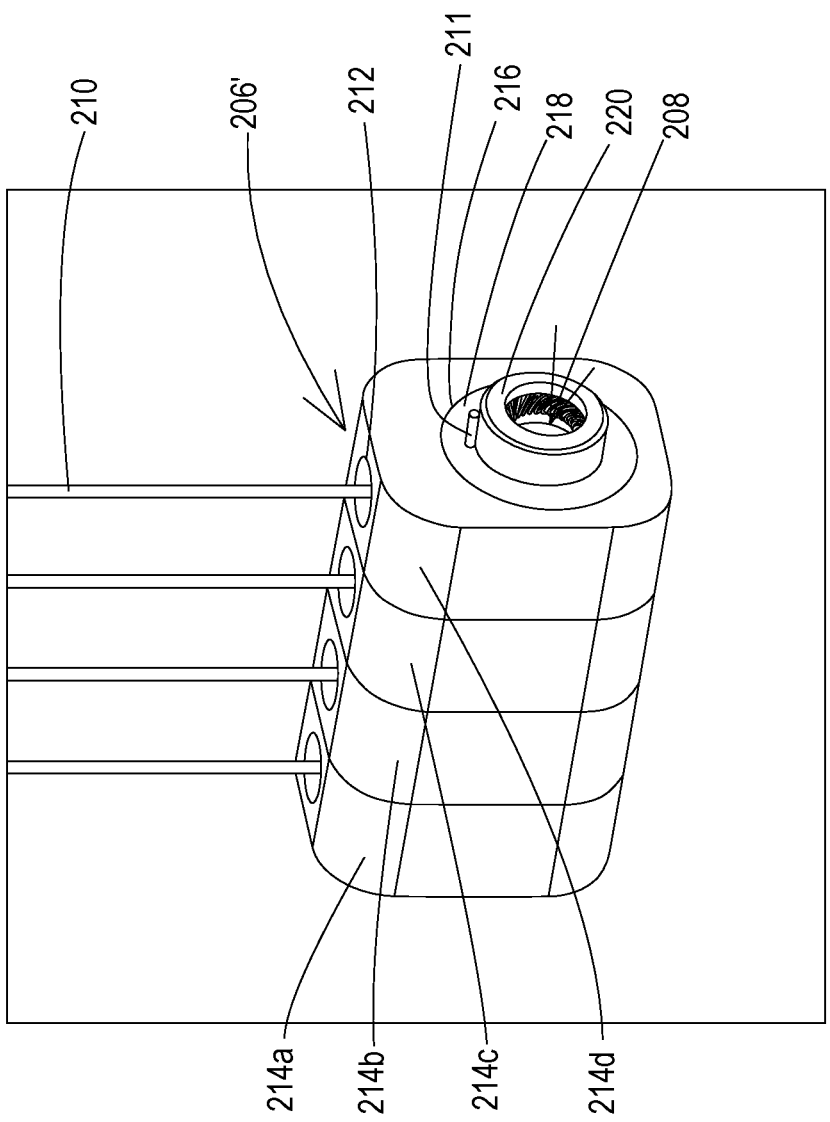
FIG. 3B shows the example of the modular lead bore including multiple lead bore modules with one lead bore module exposed for purposes of illustration.
Figure 4:
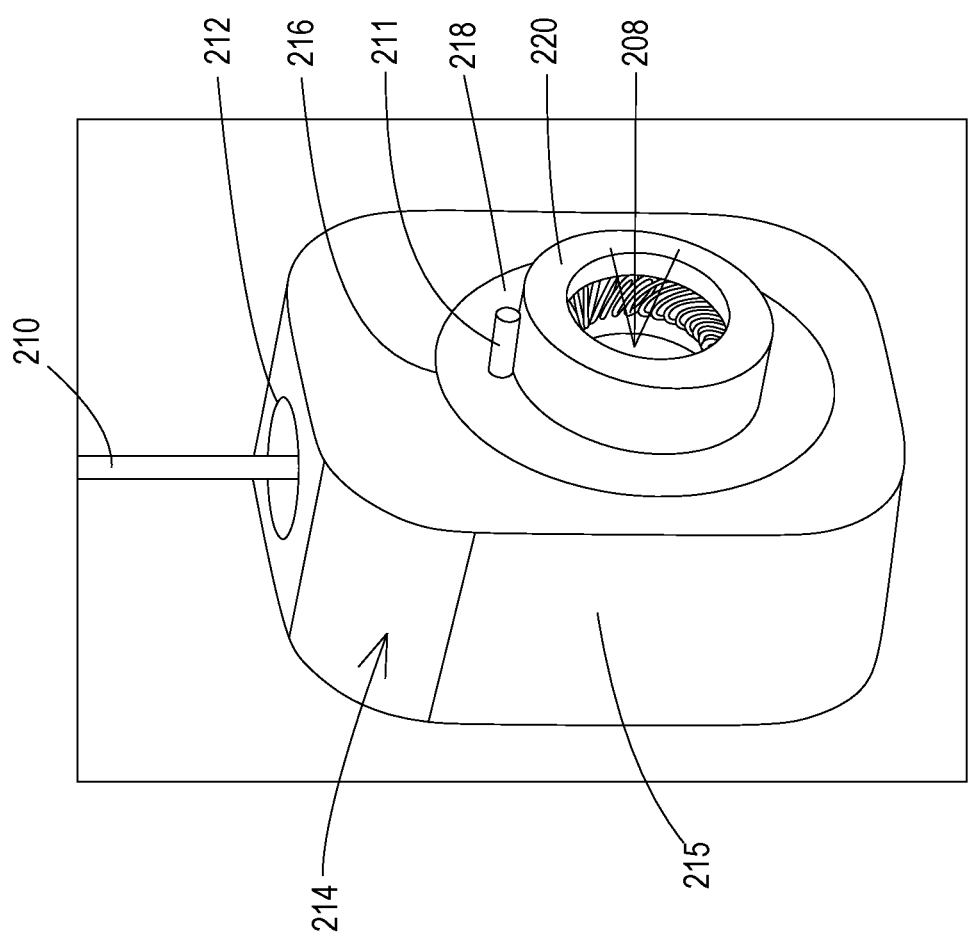
FIG. 4 shows an example of a single lead bore module that may be combined with others to form the modular lead bore.
Figure 5:
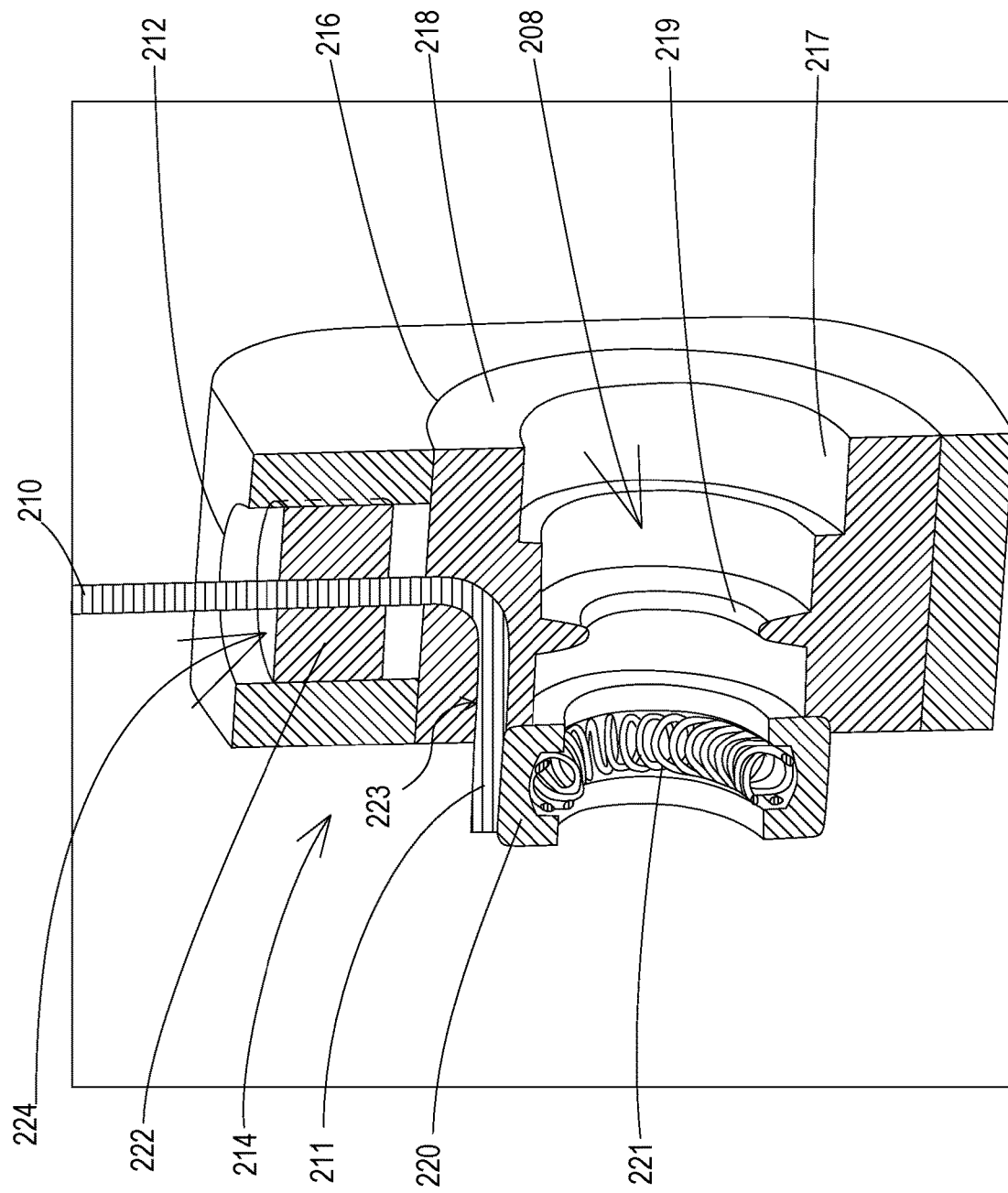
FIG. 5 shows a cross-sectional view of the single lead bore module of FIG. 4.
Figure 6:
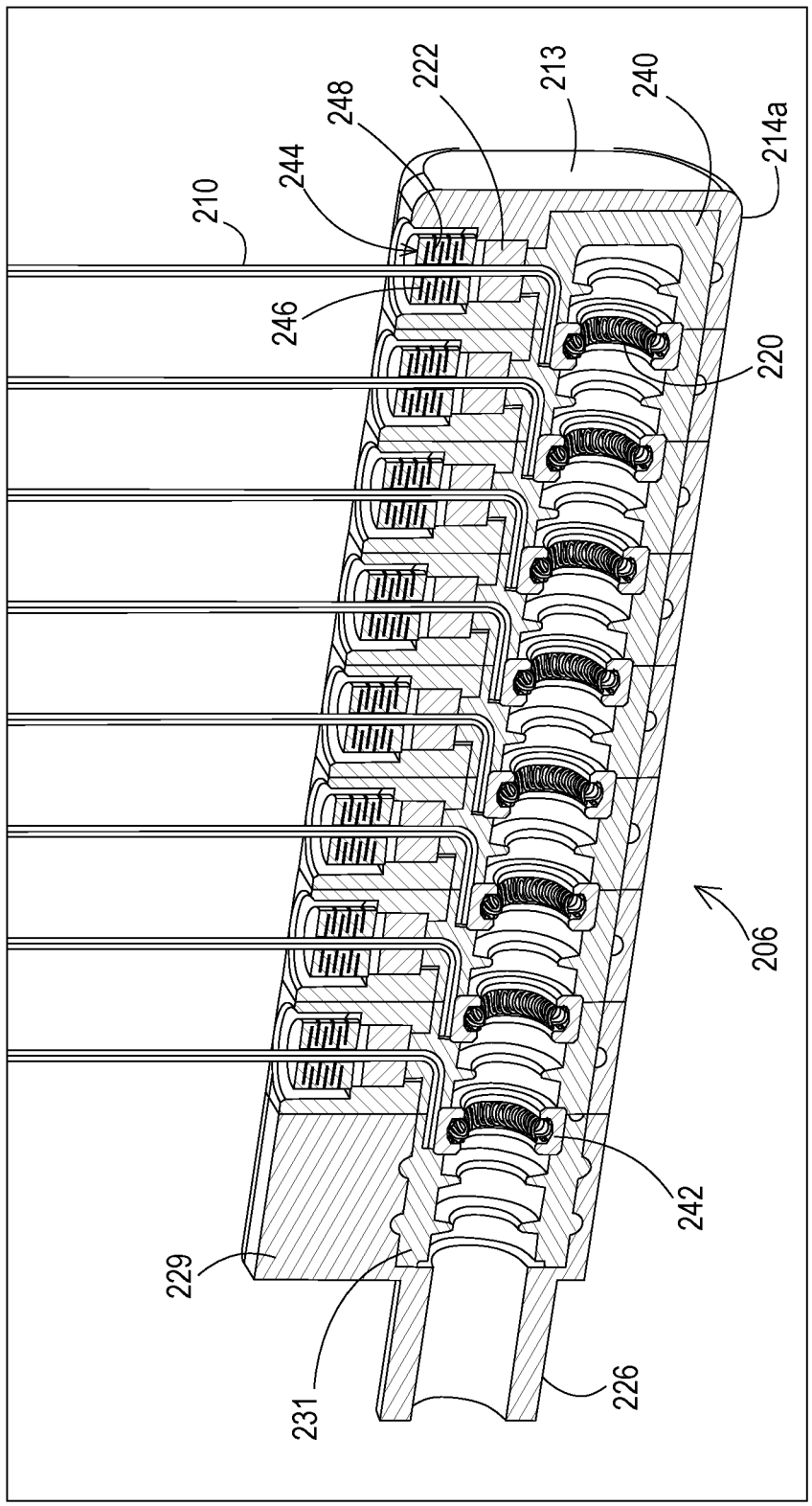
FIG. 6 shows a cross-sectional view taken along a longitudinal cut of an example of the module lead bore including multiple lead bore modules with an end module providing a hermetic termination and with a filtered feedthrough capacitor.
Figure 7:
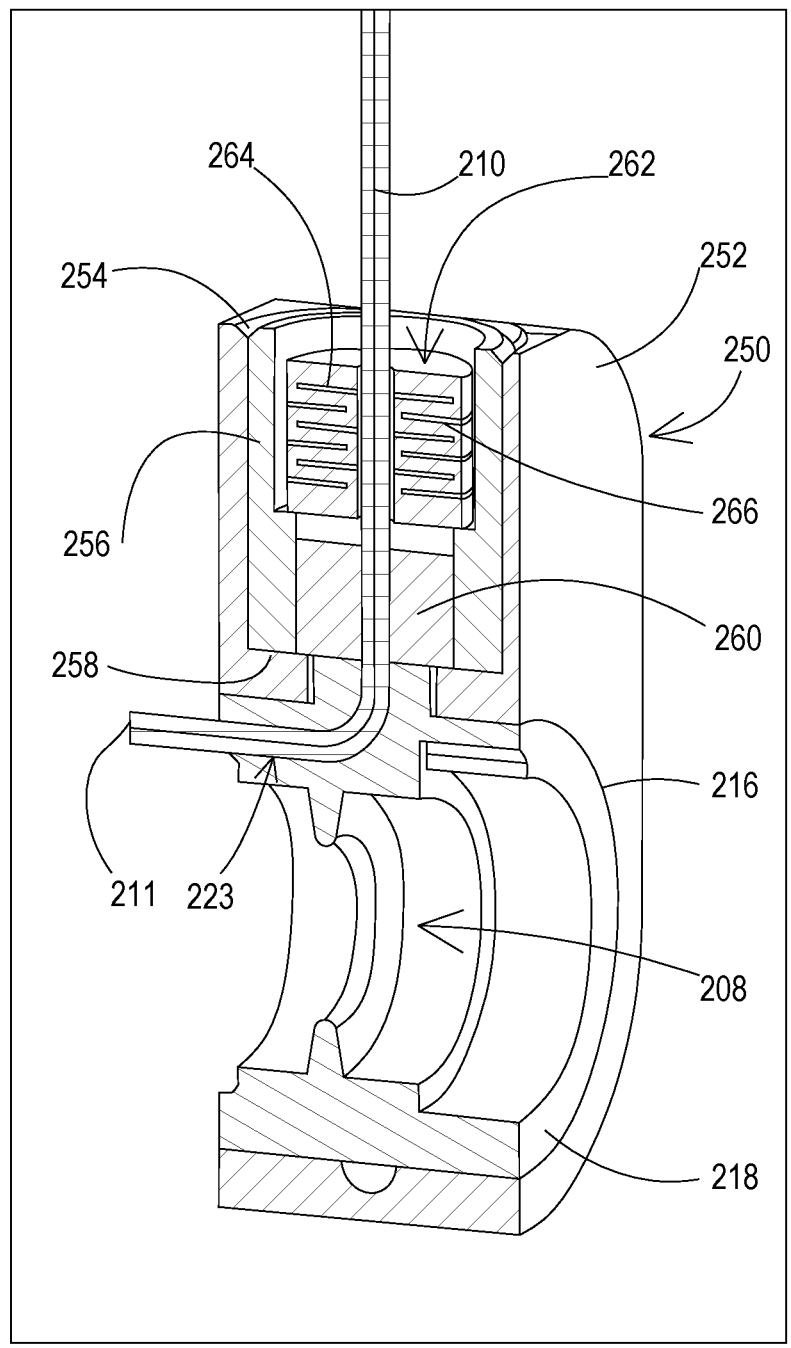
FIG. 7 shows a cross-sectional view of a single lead bore module that may be included with others to form the modular lead bore and includes a stand-alone feedthrough assembly that includes a filtered feedthrough capacitor.

Modular lead bore assemblies such as modular lead bore assemblies 206a, 206b from FIG. 2 are shown in more detail as a modular lead bore 206 of FIGS. 3A, 3B, and 6. An individual lead bore module 214 having a lead bore module body 215 is shown in FIGS. 4, 5, and 7. As shown in FIG. 3A, this example of the modular lead bore assembly 206 includes several lead bore modules such as lead bore module 214a, although lead bore module 214a is unique in that it provides a termination of the lead bore by having a wall 213. This example of the modular lead bore 206 also includes a module 229 on the opposite end from the module 214a where the module 229 does not have a feedthrough assembly but does provide a transition to the tube 226. As discussed above, in some examples, the tube 226 may be omitted and the module 229 may be directly hermetically coupled to the front wall 203 of the outer enclosure 202.

A lead bore assembly subset 206' is shown in FIG. 3B and includes a subset of lead bore modules for purposes of illustrating additional details. As shown, the subset includes four lead bore modules 214a, 214b, 214c, and 214d. During construction of the medical device, each of the lead bore modules 214a, 214b, 214c, 214d, and so on may be welded to the immediately adjacent lead bore module to form a bond between each of the lead bore modules that hermetically couples each of the lead bore modules 214 together.

Each lead bore module 214 includes various features. A feedthrough passageway 212 is present in the body of each lead bore module with a feedthrough pin 210 passing through the feedthrough passageway 212. A lead bore passageway 216 is present within each lead bore module 214, and a seal 218 resides within the lead bore passageway 216 and contacts the surface of the lead bore passageway 216 as shown in the cross-sectional view FIG. 5 which provides a cross-sectional perspective that is rotated approximately 180 degrees from that of FIG. 4. The seal 218 may include features such as a wiper seal 219 that wipes the lead body 112 as the proximal end 103 is being inserted to reduce the amount of body fluid or other debris that may enter the lead bore 208.

The seal 218 also includes a contact section 217 where an electrical contact can at least partially reside. In the example of FIG. 5, the electrical contact that partially resides in section 217 corresponds to an adjacent lead bore module where the feedthrough pin of the adjacent lead bore module is coupled to this electrical contact. An electrical contact 220 that corresponds to the lead bore module 214 of FIGS. 4 and 5 resides on the opposite side of the seal 218 from the seal section 217. This manner of construction can best be seen in the cross-sectional view of a modular lead bore 206 in FIG. 6 which is discussed in further detail below. The seal section 217 of this example shown in FIGS. 4 and 5 may accommodate the electrical contact 220 by having the electrical contact 220 create a compression fit against the seal 218 or by the seal having an additional seal portion that the contact 220 partially resides within, in addition to partially residing within the seal section of the adjacent lead bore module's seal. As can be seen, the position of the electrical contact 220 is aligned with the lead bore passageway 216, and the lead bore passageway is further aligned with the tube 226 and opening 209 (FIG. 2) so that the proximal end 103 of the lead 104 slides through the opening 209, tube 226, seal 218, and electrical contact 220 such that the proximal connector 107 makes electrical connection to the contact 220.

In this example, the feedthrough pin 210 has an end 211 that is electrically coupled to the electrical contact 220, such as by creating an electrically conductive physical coupling via a weld. It will be appreciated that in other examples, rather than the feedthrough pin 210 connecting to the electrical contact 220, the feedthrough pin could instead bend in the opposite direction and electrically couple to an electrical contact that resides in the seal section 217. In either case, the seal 218 provides a tunnel 223 that the feedthrough pin 210 passes through to reach the electrical contact 220. While the electrical contact 220 is shown as having a canted coil 221 to establish contact with the proximal connectors 107 of the lead 104, it will be appreciated that other types of electrical contacts are also applicable within the lead bore modules 214 of the modular lead bore 208. Additionally, it will be appreciated that while the example shows the lead bore modules 214a, 214b, 214c, 214d, and so on in a linear alignment, embodiments can allow for the lead bore modules to be orientated in any direction with respect to each other as desired for the particular device design.

The feedthrough pin 210 exits the lead bore module 214 by passing through the feedthrough passageway 212. However, to maintain hermeticity, a hermetic feedthrough assembly 224 must be formed within the feedthrough passageway 212 in relation to the feedthrough pin 220. In this example, the hermetic feedthrough assembly 224 includes a glass collar 222 that bonds to both the wall of the feedthrough passageway 212 and to the feedthrough pin 210. The glass collar 222 forms a hermetic seal against both the feedthrough passageway wall and feedthrough pin 210 such that the hermeticity is maintained and any body fluid present within the modular lead bore 208 cannot pass through the feedthrough passageway 212.

FIG. 6 shows an example of the module lead bore 206 where the feedthrough assemblies provide a filtered feedthrough. The filtered feedthrough is established by include a filtering capacitor 244 which in this example resides within feedthrough passageway and on the opposite side of the glass collar 222 from the electrical contact 220. The filtering capacitor 244 includes multiple plates where at least one plate 246 is exposed to the pin 210 and where at least one other plate 248 is exposed to the module body 215 of each lead bore module 214, such as lead bore module 214a. Solder or another sufficiently electrically conductive medium may be added in the space between the capacitor 244 and the module body 215 and in the space between the capacitor 244 and the pin 210. The solder completes an electrical pathway from the plate 246 to the pin 210 and from the plate 248 to the body 215. The size and amount of overlap of the plates 246, 248, the space between the plates 246 and 248, and the dielectric material of the capacitor 244 that is present between the plates 246 248 contribute to the resulting capacitance.

The cross-sectional view of the modular lead bore assembly 206 of FIG. 6 also shows additional aspects. It can be seen that one end of the lead bore is formed by the module 229. The module 229 houses an end seal 231 that abuts the last electrical contact 242. The module 229 also provides the tube 226 as an integral feature in this example. On the opposite end of the lead bore, it can be seen that the first module 214a houses a unique seal 240 that provides a seal wall adjacent to the module wall 213 that terminates the lead bore.

FIG. 7 shows another example of a lead bore module 250. The lead bore module 250 includes features like the lead bore module 214 shown in FIGS. 4-6 including a module body 252, the seal 218, and the tunnel 223. The same electrical contact 220 is also included in the same manner as shown in FIGS. 4-6 but is omitted from this particular view in FIG. 7.

However, in the lead bore module 250 of FIG. 7, the feedthrough assembly has a different construction from that of the lead bore module 214. A feedthrough passageway 254 formed in the module body 252 allows for a stand-alone feedthrough module to be used. In this example, the feedthrough passageway 254 includes a ledge 258 that the stand-alone feedthrough assembly may rest upon.

The stand-alone feedthrough assembly of FIG. 7 includes a ferrule 256 and the pin 210 passing through the ferrule 256. A glass collar 260 is hermetically bonded to both the ferrule 256 and the pin 210. Upon installing the stand-alone feedthrough assembly, the ferrule 256 may be positioned within the passageway 254 and then welded in place. The pin 210 may be bent to form the end 211 that the tunnel 223 may then accept as the seal 218 is installed into the module body 252.

This stand alone feedthrough assembly of FIG. 7 may also provide the filtered feedthrough by including a filtering capacitor 262 which in this example resides within feedthrough passageway and on the opposite side of the glass collar 260 from the seal 218. The filtering capacitor 262 includes multiple plates where at least one plate 264 is exposed to the pin 210 and where at least one other plate 266 is exposed to the ferrule 256. Solder may be added in the space between the capacitor 262 and the ferrule 256 and the space between the capacitor 262 and the pin 210. The solder completes an electrical pathway from the plate 264 to the pin 210 and from the plate 266 to the ferrule 256. The bond of the ferrule 256 to the module body 252 thereby continues the electrical pathway to the module body 252. The size and amount of overlap of the plates 264, 266, the space between the plates 264 and 266, and the dielectric material of the capacitor 262 that is present between the plates 264 and 266 contribute to the resulting capacitance.

The lead bore module bodies 215, 252 of the examples shown in FIGS. 3A-7 may be constructed of various materials, such as titanium, tantalum, niobium, alloys of titanium including titanium-niobium alloys, various grades of stainless steel, and the like. These materials allow for the hermetic bond to be formed between individual lead bore modules 214, 250 and for the glass collar 222 to bond to the wall of the feedthrough passageway 212. Additionally, because the lead bore modules 214 are electrically isolated from the electrical contacts 220 and feedthrough pins 210, the lead bore modules 214 may be mounted within the enclosure 202 such as by being welded in place against the enclosure 202 forming a hermetic joint.

The seals 218 as well as the unique end seals 231 and 240 mentioned above, the feedthrough pins 210, and the electrical contacts 220 may all be constructed with conventional materials for those respective purposes. For example, the seals 218, 231, and 240 may be constructed of materials such as liquid silicone rubber and the like while the feedthrough pins 210 are constructed of materials such as titanium, tantalum, niobium, alloys of titanium including titanium-niobium alloys, platinum, alloys of platinum including platinum-iridium alloys, and the like. Also for example, the electrical contacts are constructed of materials such as MP35N® alloy, platinum-iridium alloy, stainless steel, and the like.

While embodiments have been particularly shown and described, it will be understood by those skilled in the art that various other changes in the form and details may be made therein without departing from the spirit and scope of the invention.

What is claimed is:

1. A modular lead bore for an implantable medical device that includes medical device circuitry, the modular lead bore comprising:
- a plurality of lead bore modules that are hermetically coupled together, each lead bore module of the plurality of lead bore modules comprising a lead bore passageway and a feedthrough passageway;
- a plurality of electrical contacts, each electrical contact of the plurality of electrical contacts being aligned to the lead bore passageway of each corresponding lead bore module;
- a plurality of seals, where each seal of the plurality is present within the lead bore passageway of each corresponding lead bore module and between electrical contacts;
- a plurality of hermetic feedthrough assemblies, each hermetic feedthrough assembly of the plurality of hermetic feedthrough assemblies being present within the feedthrough passageway of each corresponding lead bore module; and
- a plurality of feedthrough pins, with each feedthrough pin of the plurality of feedthrough pins passing through the hermetic feedthrough assembly of each corresponding lead bore module, each feedthrough pin being electrically coupled to the electrical contact of each corresponding lead bore module and being configured to couple to the medical device circuitry.

2. The modular lead bore of claim 1, wherein the lead bore modules are constructed of a metal and are welded together.

3. The modular lead bore of claim 1, wherein each hermetic feedthrough assembly comprises a glass collar within the corresponding feedthrough passageway, each glass collar being bonded against the corresponding lead bore module and the corresponding feedthrough pin.

4. The modular lead bore of claim 1, further comprising a header defining a lead bore opening that is aligned with the lead bore passageway of the plurality of lead bore modules, the header being coupled to the housing.

5. The modular lead bore of claim 4, wherein the lead bore passageway comprises a tube that extends from the lead bore opening of the header to the lead bore module, the tube being coupled directly to a first lead bore module of the plurality.

6. The modular lead bore of claim 5, wherein the tube is welded to the first lead bore module.

7. The modular lead bore of claim 1, wherein each hermetic feedthrough assembly comprises a filtering capacitor creating a capacitive coupling between the pin and a body of the corresponding lead bore module.

8. The modular lead bore of claim 1, wherein each hermetic feedthrough assembly comprises a ferrule that contacts a body of the corresponding lead bore module.

9. A method of constructing a modular lead bore, comprising:
- hermetically coupling a plurality of lead bore modules together, each lead bore module comprising a lead bore passageway and a feedthrough passageway;
- providing a plurality of electrical contacts with each electrical contact of the plurality of electrical contacts being present within the lead bore passageway of each corresponding lead bore module;
- providing a plurality of seals, where each seal of the plurality of seals is present the lead bore passageway of each corresponding lead bore module and is present between electrical contacts;
- providing a plurality of hermetic feedthrough assemblies, each hermetic feedthrough assembly of the plurality of hermetic feedthrough assemblies being present within the feedthrough passageway of each corresponding lead bore module; and
- providing a plurality of feedthrough pins, each feedthrough pin of the plurality of feedthrough pins passing through the hermetic feedthrough assembly of each corresponding lead bore module, each feedthrough pin of the plurality of feedthrough pins being electrically coupled to the electrical contact of each corresponding lead bore module and being configured to couple to medical device circuitry.

10. The method of claim 9, wherein the lead bore modules are constructed of a metal.

11. The method of claim 10, where the lead bore modules are welded together.

12. The method of claim 9, wherein each hermetic feedthrough assembly comprises a glass collar within the feedthrough passageway, the glass collar being bonded against the lead bore module and the feedthrough pin.

13. The method of claim 9, wherein the lead bore passageway of the plurality of lead bore modules is configured to align with a lead bore opening of a header of the medical device.

14. The method of claim 9, wherein each hermetic feedthrough assembly comprises a filtering capacitor creating a capacitive coupling between the pin and a body of the corresponding lead bore module.

15. The method of claim 9, wherein each hermetic feedthrough assembly comprises a ferrule that contacts a body of the corresponding lead bore module.

* * * * *